United States Patent
Chen et al.

(10) Patent No.: US 10,379,067 B2
(45) Date of Patent: Aug. 13, 2019

(54) METHOD AND SYSTEM FOR LIQUID DETECTION

(71) Applicants: Tsinghua University, Beijing (CN); Nuctech Company Limited, Beijing (CN)

(72) Inventors: Zhiqiang Chen, Beijing (CN); Li Zhang, Beijing (CN); Tianyi Yang Dai, Beijing (CN); Ji Zhao, Beijing (CN); Xin Jin, Beijing (CN); Ming Chang, Beijing (CN)

(73) Assignees: Tsinghua University, Beijing (CN); Nuctech Company Limited, Beijing (CN)

( * ) Notice: Subject to any disclaimer, the term of this patent is extended or adjusted under 35 U.S.C. 154(b) by 254 days.

(21) Appl. No.: 15/257,595

(22) Filed: Sep. 6, 2016

(65) Prior Publication Data

US 2017/0176351 A1  Jun. 22, 2017

(30) Foreign Application Priority Data

Dec. 18, 2015 (CN) .......................... 2015 1 0958981

(51) Int. Cl.
*G01N 23/00* (2006.01)
*G01N 23/046* (2018.01)
(Continued)

(52) U.S. Cl.
CPC ............ *G01N 23/046* (2013.01); *G01N 23/20* (2013.01); *G01N 23/20083* (2013.01);
(Continued)

(58) Field of Classification Search
CPC ....... G01N 2223/056; G01N 2223/316; G01N 2223/419; G01N 2223/637; G01N 23/046;
(Continued)

(56) References Cited

U.S. PATENT DOCUMENTS

| 7,486,760 B2 | 2/2009 | Harding |
| 7,924,978 B2 | 4/2011 | Harding |

(Continued)

FOREIGN PATENT DOCUMENTS

| CN | 102253065 | 12/2014 |
| CN | 104949910 A | 9/2015 |
| WO | WO 2014/124522 | 8/2014 |

OTHER PUBLICATIONS

Extended European Search Report dated Apr. 12, 2017 in EP Application No. 16186296.6 (12 pages).
(Continued)

*Primary Examiner* — Irakli Kiknadze
(74) *Attorney, Agent, or Firm* — Knobbe, Martens, Olson & Bear LLP (57) ABSTRACT

Systems and methods for liquid detection are disclosed. An illustrative method for liquid detection herein may include implementing CT imaging and XRD imaging on one or more liquid planes of liquid contained in a container at once by rotating the container so that X-rays from a same radiation source scan a whole area of each of the one or more liquid planes, and generating a substance identification result for the liquid contained in the container based on a CT image and a XRD image, wherein the CT imaging and the XRD imaging are implemented on a same liquid plane or different liquid planes. Consistent with various aspects and features, implementations may identify substances contained in the liquid more quickly and accurately.

18 Claims, 7 Drawing Sheets

(51) Int. Cl.
  *G01N 23/20* (2018.01)
  *G21K 1/02* (2006.01)
  *G01V 5/00* (2006.01)
(52) U.S. Cl.
  CPC ............ *G01V 5/0016* (2013.01); *G21K 1/02* (2013.01); *G01N 2223/056* (2013.01); *G01N 2223/316* (2013.01); *G01N 2223/419* (2013.01); *G01N 2223/637* (2013.01)
(58) Field of Classification Search
  CPC ............ G01N 23/20; G01N 23/20083; G01N 2223/629; G01N 2223/66; G01N 23/207; G01N 23/201; G01N 2223/639; G01N 2223/045; G01N 2223/643; G01N 23/083; G01N 23/2076; G01N 23/04; G01N 2223/308; G01N 2223/421; G01N 2223/1016; G01N 23/087; G01N 23/10; G01N 2223/206; G01N 2223/401; G01N 2223/601; G01N 23/06; G01N 23/203; G01N 24/084; G01V 5/0016; G01V 5/00; G01V 5/0025; G01V 5/005; G01V 5/0041; G21K 1/02; G21K 2207/00; G06T 11/008; G06T 2207/10112; G06T 2207/10116

USPC ............................ 378/4, 6, 7, 16, 57, 62, 70
  See application file for complete search history.

(56) References Cited

U.S. PATENT DOCUMENTS

| | | |
|---|---|---|
| 2009/0323889 A1* | 12/2009 | Harding .................. G01V 5/00 378/9 |
| 2010/0166285 A1 | 7/2010 | Schlomka et al. |
| 2011/0188632 A1 | 8/2011 | Harding et al. |
| 2011/0200164 A1 | 8/2011 | Blaj |
| 2012/0133516 A1 | 5/2012 | Harding |
| 2013/0251100 A1 | 9/2013 | Sasaki et al. |
| 2016/0018557 A1* | 1/2016 | Yi ....................... G01V 5/0008 356/301 |

OTHER PUBLICATIONS

International Search Report and Written Opinion dated Nov. 16, 2016 in PCT Application No. PCT/CN2016/095059 (12 pgs), and English-language translation of ISR (2 pgs); 14 pages total.
Office Action issued in Chinese Patent Application No. 201510958981.5, dated Dec. 4, 2018.

* cited by examiner

METHOD AND SYSTEM FOR LIQUID DETECTION

CROSS-REFERENCE TO RELATED APPLICATIONS

This application is based upon and claims benefit/priority of Chinese Patent Application No. 201510958981.5, filed on Dec. 18, 2015, published as CN 106896122 A, which are incorporated herein by reference in entirety.

BACKGROUND

Field

The invention generally relates to substance identification, and more particularly to a method and system for liquid detection.

Description of Related Information

In traditional radiation imaging, a primary method to achieve nondestructive detection is diffraction imaging, which realizes noninvasive detection of liquid substance based on a principle that substances of different molecular structures may have different X-ray diffraction (XRD) patterns.

OVERVIEW OF SOME ASPECTS

A method and system for liquid detection, a primary collimator and a scattering collimator used in the system for liquid detection are provided consistent with the innovations herein.

An illustrative method for liquid detection according to embodiments of the inventions herein may comprise: implementing CT imaging and XRD imaging on one or more liquid planes of liquid contained in a container by rotating the container so that X-rays from a same radiation source scan a whole area of each of the one or more liquid planes; and generating a substance identification result for the liquid contained in the container based on a CT image and a XRD image, wherein the CT imaging and the XRD imaging are implemented on a same liquid plane or different liquid planes.

An illustrative system for liquid detection according to one or more embodiments of the present innovations may comprise a radiation source configured to emit X-rays; a primary collimator provided at the downstream of the radiation source and configured to form X-rays for CT imaging and X-rays for XRD imaging from the X-rays from the radiation source; a CT imaging apparatus configured to implement CT imaging by utilizing the X-rays for CT imaging; a XRD imaging apparatus configured to implement XRD imaging by utilizing the X-rays for XRD imaging; and a carrying apparatus configured to rotate a container containing liquid, so that the X-rays from the radiation source scan a whole area of each of one or more liquid planes of the liquid contained in the container, wherein the CT imaging apparatus and the XRD imaging apparatus implement the CT imaging and the XRD imaging on the one or more liquid planes at the same time, and a CT image and a XRD image are utilized to generate a substance identification result for the liquid contained in the container.

A scattering collimator used in a system for liquid detection according to one or more embodiments of the present innovations may comprise an aperture at a center; and a plurality of circular-arc slits taking the aperture as their center, wherein radiuses of the plurality of circular-arc slits are the same of different.

A primary collimator used in a system for liquid detection according to embodiments of the present innovations may comprise a CT slit or apertures for forming X-rays for CT imaging; and XRD apertures for forming X-rays for XRD imaging, wherein the CT slit or apertures and the XRD apertures are on a same straight line within a same plane or on two different straight lines at a predetermined distance away from each other within the same plane.

Methods and systems for liquid detection according to the embodiments of the present innovations may implement CT detection and XRD detection on one or more liquid planes at the same time by utilizing the same radiation source, so substances contained in the liquid may be identified quickly and accurately.

BRIEF DESCRIPTION OF THE DRAWINGS

The invention may be better understood from the following descriptions of the embodiments of the invention in conjunction with the accompany drawings, wherein.

DETAILED DESCRIPTION OF ILLUSTRATIVE IMPLEMENTATIONS

Exemplary embodiments and features of various aspects consistent with the present innovations will be described in detail below. In the detailed descriptions, a number of specific details are described to provide a complete understanding of the invention. However, it is obvious to the person skilled in the art that the invention may be practiced without some of these specific details. The following descriptions of the embodiments merely intend to provide better understanding of the invention by illustrating examples of the invention. The invention is not limited to any specific configuration and algorithm set forth below, but intends to cover all modifications, substitutions, and improvements of elements, components and algorithms without departing from the spirit of the present inventions. In the drawings and the descriptions below, well known structures and techniques are not shown to avoid unnecessarily obscuring the invention.

For liquid security checking, how to identify prohibited substances contained in liquid is a core part. Traditional prospective imaging techniques, for example, dual-energy computerized tomography (CT)/multi-energy CT, have limitations that lead to a high rate of false alarm. Existing XRD detection techniques are highly capable of substance identification and may effectively improve detection accuracy in combination with dual-energy CT/energy spectrum CT, but still have many problems.

In one aspect, XRD signals are weak and the detection efficiency thereof is relatively low. In existing XRD detection techniques, the employment of a conical scattering structure design may effectively improve signal strength; however, since this design is based on point-by-point detection, in which relative movements between a detector and a radiation source in a plurality of directions are required in order to scan a whole plane to be detected, the detection efficiency is relatively low. In other approaches to improve the detection efficiency of XRD detection, the amount of detectors and radiation sources to be used increases, and the design and processing difficulty of primary and scattering collimators are high, leading to a high cost. Currently, there is no small-scale XRD detection system with high efficiency, high quality and low cost for liquid detection.

In another aspect, in existing liquid security checking techniques, in order to improve the detection accuracy, a multi-stage detection strategy, in which CT/dual-energy CT/multi-energy CT and XRD is combined, may be employed. This makes the whole system for XRD detection suffer from complicated operation, reduced efficiency, increased size, and at the same time a high cost.

In view of one or more deficiencies existing in the liquid detection techniques described above, the invention provides a novel method and system for liquid detection. Here, in order to identify substances contained in liquid more accurately, DR, CT and XRD will be used in combination. The method and system for liquid detection according to embodiments of the invention will be described in detail below in combination with the accompany drawings.

Figure 1:
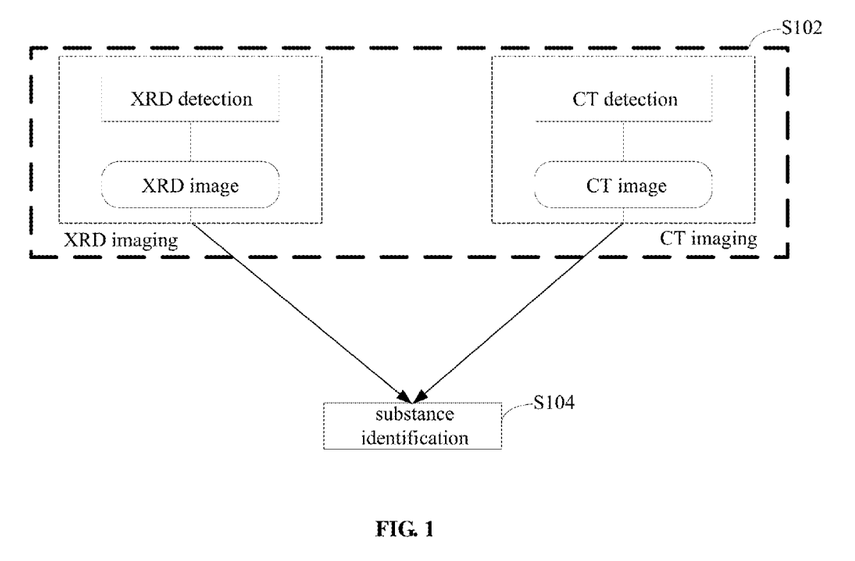
FIG. 1 is a flow diagram illustrating a method for liquid detection according to one or more embodiments consistent with aspects of the innovations herein.

FIG. 1 is a flow diagram illustrating a method for liquid detection according to embodiments of the invention. As illustrated in FIG. 1, the method for liquid detection includes: S102, CT imaging and XRD imaging are implemented simultaneously on one or more liquid planes of liquid contained in a container by rotating the container so that X-rays from a same radiation source scan a whole area of each of the one or more liquid planes; and S104, a substance identification result for the liquid contained in the container is generated based on a CT image and a XRD image, wherein the CT imaging and the XRD imaging may be implemented on a same liquid plane or different liquid planes. In this embodiment, DR imaging may be implemented prior to the CT imaging and the XRD imaging so that the one or more liquid planes may be selected based on a DR image. In other embodiments, the one or more liquid planes may also be specified by a user as required. As CT detection and XRD detection are implemented on the one or more liquid planes, the one or more liquid planes may also be referred as CT detection planes and/or XRD detection planes.

Figure 2:
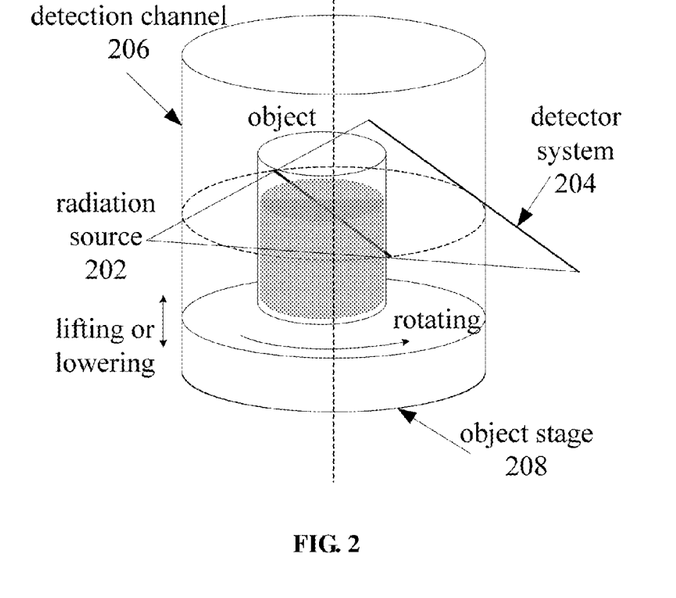
FIG. 2 is a structural diagram illustrating a system for liquid detection according to one or more embodiments consistent with aspects of the innovations herein.

FIG. 2 is a structural diagram illustrating a system for liquid detection according to embodiments of the invention. As illustrated in FIG. 2, the system for liquid detection includes a radiation source 202, a detector system 204, a detection channel 206, and an object stage 208, wherein: the radiation source 202 may be a single point radiation source or a distributed radiation source provided external to the detection channel 206; the detector system 204 is provided external to the detection channel 206 on the opposite side of the radiation source 202 and includes a CT detector part and a XRD detector part; the detection channel 206 is provided between the radiation source 202 and the detector system 204; the object stage 208 is provided within the detection channel 206 and is used to lift/descend or rotate an object being carried by it.

In particular, the XRD detector part may be used to receive transmitted photons and scattered photons and may include one or more XRD detection/scattering collimation modules; the CT detector part may include one or more CT detectors; a primary collimator is provided at the downstream of the radiation source 202; the XRD detection/scattering collimation module includes a XRD detector and a scattering collimator; the scattering collimator is provided at the upstream of the XRD detector, so that X-rays satisfying a certain geometrical condition may be detected by the XRD detector.

The system for liquid detection according to embodiments of the invention may implement DR imaging, XRD imaging, and CT/dual-energy CT/energy spectrum CT imaging (for simplicity, CT imaging, dual-energy CT imaging and energy spectrum CT imaging are collectively referred as CT imaging), and thus accurately identify the substances contained in the liquid. Specifically, when a container containing liquid is placed at the object stage 208, the object stage 208 carrying the container may descend along the detection channel 206, during which DR imaging may be implemented. An intermediate liquid plane may be selected automatically based on a DR image, or an inspector may be promoted to manually select a liquid plane; the object stage 208 is adjusted to lift/descend, so that the selected liquid plane is adjusted to the XRD/CT detection plane. In the embodiment illustrated in FIG. 2, the XRD detection plane and the CT detection plane are the same detection plane, i.e., the selected liquid plane. While the radiation source 202 emits X-rays, the detector system 204 receives data, and the object stage 208 carrying the container rotates, thereby the selected liquid plane is scanned and the XRD image and the CT image are obtained. The substance identification result for the liquid may be generated by combining the XRD image and the CT image. Here, the DR imaging may be implemented by utilizing the CT detector part. The highest liquid plane may be identified based on the DR image, and the intermediate liquid plane for subsequent XRD detection and CT detection may be selected automatically or manually.

Figure 3:
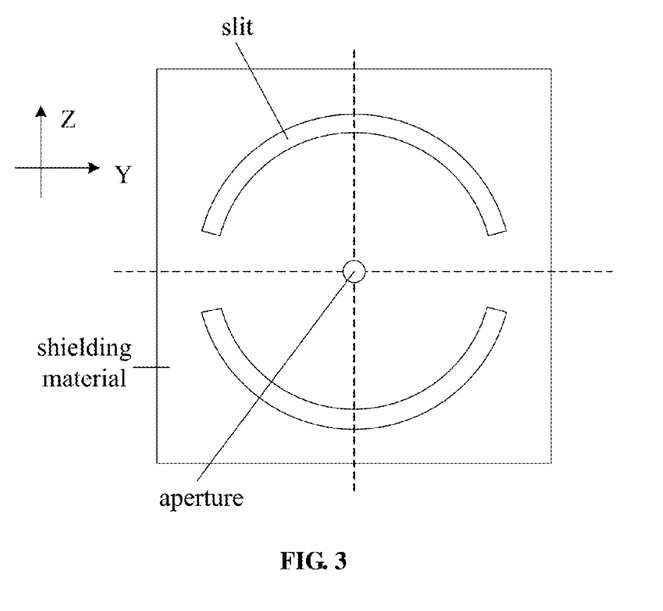
FIG. 3 is a schematic diagram illustrating a scattering collimator used in the system for liquid detection illustrated in FIG. 2, according to one or more aspects consistent with innovations herein.

FIG. 3 is a schematic diagram illustrating a scattering collimator used in the system for liquid detection illustrated in FIG. 2. In any XRD detection/scattering collimation module, a relative position of the scattering collimator and the XRD detector is fixed, both the scattering collimator and the XRD detector facing an incident ray distributed within the XRD detection plane. The scattering collimator is made of materials with high X-ray shielding ability, for example, tungsten. As shown in FIG. 3, the scattering collimator mainly includes two parts: slits and an aperture. The aperture at the center of the scattering collimator is opposite to a transmitted ray that is collinear with the incident ray, and the transmitted ray may pass through the aperture to get into the XRD detector, so that the transmitted energy spectrum may be measured. There are two circle arcs with different radiuses, both taking the aperture as their center. Different radiuses correspond to different scattering angles, and the two circle arcs may correspond to the same radius or different radiuses. The two circle-arc slits are disconnected to each other near the Y-axis, one reason is for the connection of the material and the other reason is to avoid interference from scattered rays of neighboring incident rays. The scattering collimator has a thickness adequate to shield unwanted incident rays, so that the XRD detector has a sufficient angular resolution.

Figure 4:
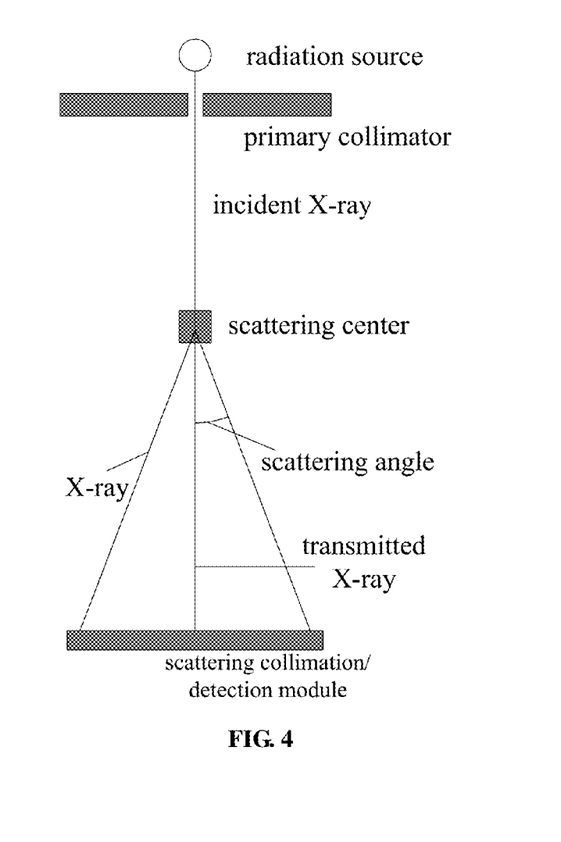
FIG. 4 is a schematic diagram illustrating XRD detection that is implemented by utilizing the scattering collimator illustrated in FIG. 3, according to one or more aspects consistent with innovations herein.

FIG. 4 is a schematic diagram illustrating XRD detection that is implemented by utilizing the scattering collimator illustrated in FIG. 3, i.e., pencil beam-cone type XRD detection. As illustrated in FIG. 4, with the limitation of the primary collimator, an incident ray for XRD detection from the radiation source forms a pencil beam ray, irradiates the object, and scatters at the scattering center. Scattered rays at a predetermined scattering angle form a cone surface with the scattering center as the vertex of the cone, the central axis is the incident ray, i.e., the transmitted ray, and the scattered rays are distributed on the cone surface, wherein the scattered rays correspond to generatrices of the cone surface. With the limitation of the scattering collimator, the XRD detector may measure the energy spectra of the scattered rays distributed on the cone surface and the transmitted ray, wherein the slit and the aperture on the scattering collimator allow the transmitted ray and the scattered rays at the predetermined scattering angle to get into the XRD detector, while other rays may be shielded. The scattering center is at a fixed position between the radiation source and the XRD detector and the fixed position is dependent on the scattering angle, the size of the scattering collimator, the size of the XRD detector, and the like.

The pencil beam-cone type XRD detection may greatly improve signal strength compared to a pencil beam-pencil beam type XRD detection, in which the incident ray and the scattered ray are both pencil beam rays and intersect with each other at a certain angle. The XRD detector only needs to output two kinds of data, i.e., the transmitted energy spectrum and the scattered energy spectrum. Here, the XRD detector may either output a summation derived by adding up the scattered energy spectra of the scattered rays on the cone surface or output separately the scattered energy spectra of the scattered rays at different generatrices of the cone surface. In this case, the XRD detector is a pixelated energy resolving detector.

Figure 5:
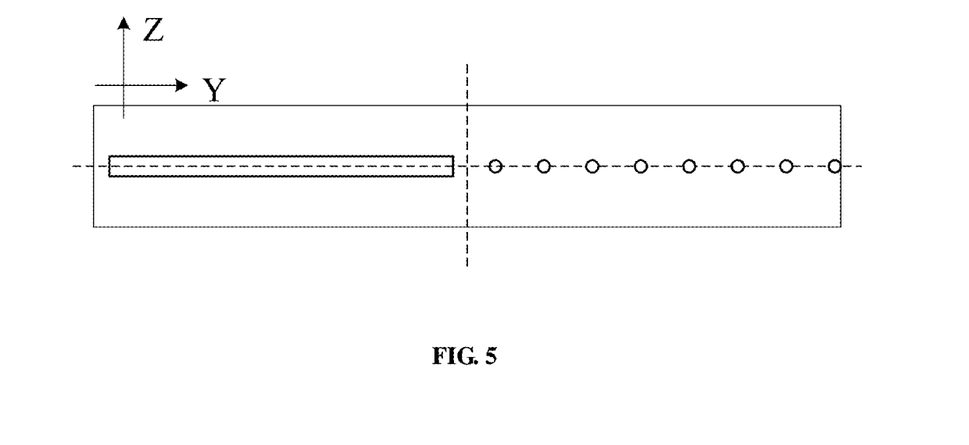
FIG. 5 is a schematic diagram illustrating a primary collimator used in the system for liquid detection illustrated in FIG. 2, i.e., the primary collimator that is utilized when XRD detection and CT detection are implemented on a same liquid plane, according to one or more aspects consistent with innovations herein.

FIG. 5 is a schematic diagram illustrating a primary collimator used in the system for liquid detection illustrated in FIG. 2, i.e., the primary collimator that is utilized when the XRD and the CT detection are implemented at a same liquid plane. As illustrated in FIG. 5, a slit (or apertures) corresponding to CT detection and apertures corresponding to XRD detection on the primary collimator are on a same straight line parallel to the Y-axis. Although the apertures corresponding to the XRD detection are equally spaced in the direction of the Y-axis, they may also be unequally spaced in the direction of the Y-axis. The primary collimator is also made of materials with high X-ray shielding ability, and has a thickness adequate to shield unwanted incident rays.

Figure 6:
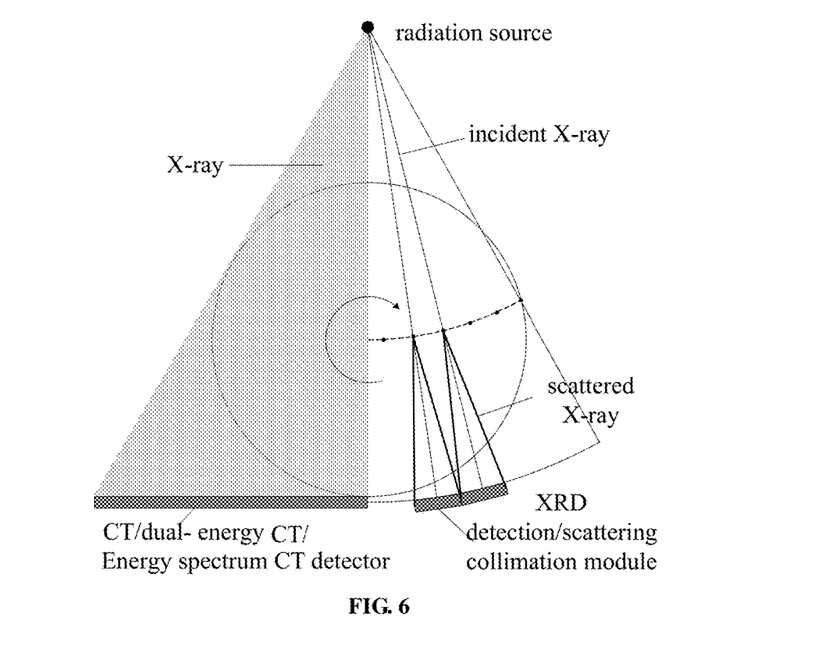
FIG. 6 is a schematic diagram illustrating XRD detection that is implemented by utilizing the scattering collimator illustrated in FIG. 3 and the primary collimator illustrated in FIG. 5, according to one or more aspects consistent with innovations herein.

FIG. 6 is a schematic diagram illustrating XRD detection that is implemented by utilizing the scattering collimator illustrated in FIG. 3 and the primary collimator illustrated in FIG. 5. As illustrated in FIG. 6, the CT detection and the XRD detection are implemented on the same detection plane. That is, the CT detection plane overlaps with the XRD detection plane, and the CT detection and the XRD detection are implemented on the selected liquid plane. The detection area in the CT/XRD detection plane is divided into two parts: a CT detection area at the left side in which the CT detection is implemented by utilizing a half-detector measuring method, and a XRD detection area at the right side in which the scattering centers are distributed. With the rotation of the container containing the liquid, complete data of both sides may be obtained.

It should be noted that although a plurality of scattering centers located in the XRD detection area on the right side of the CT/XRD detection plane are distributed on an arc, the plurality of scattering centers may also be distributed on a straight line passing through the rotational center of the object stage or on other curves in practice. Here, the specific positions of the scattering centers depend on the geometric position, relative position, and size of the apertures corresponding to the XRD detection on both the XRD detection/scattering collimation module and the primary collimator. In addition, neighboring scattering centers (i.e., measuring points) may either be equally or unequally spaced.

Although it is illustrated in FIG. 2 through FIG. 6 that the XRD detection and the CT detection are implemented on the same detection plane, i.e., the XRD detection and the CT detection are implemented on the selected liquid plane, the XRD detection and the CT detection may actually be implemented on two different liquid planes that are respectively below and above the liquid plane that is selected based on the DR image. In view of the uniformity of liquid, the XRD detection and the CT detection may be regarded as being implemented with respect to the same substance though they are implemented on different liquid planes. The XRD detection plane may be above and/or below the CT detection plane. That is to say, there may be one or more CT detection planes and/or one or more XRD detection planes. If the CT detection and the XRD detection are implemented on different detection planes, the upper and lower circle arcs on the scattering collimator illustrated in FIG. 3 may also be disconnected near the Z-axis, so that scattering interference from incident rays for CT detection may be effectively avoided when the CT detection plane is close to the XRD detection plane.

Figure 7:
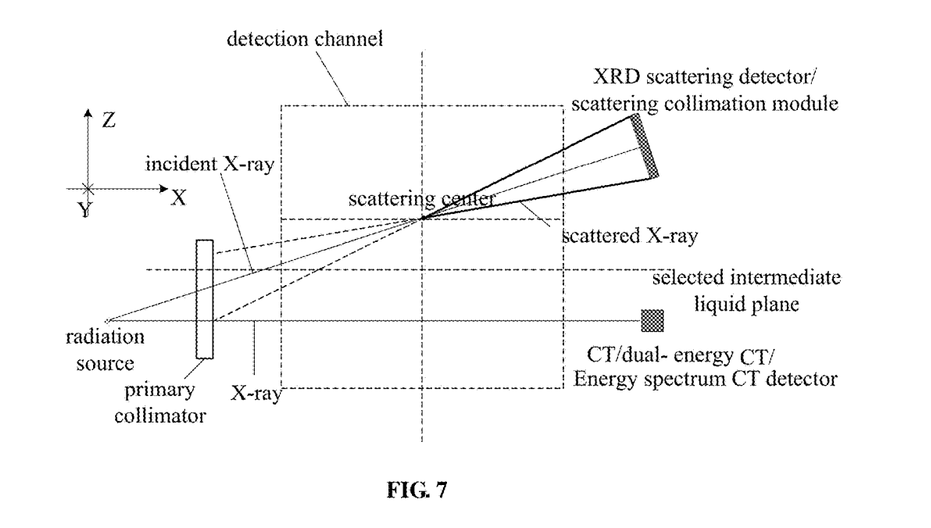
FIG. 7 is a schematic diagram illustrating XRD detection and CT detection that are implemented on two different liquid planes, according to one or more aspects consistent with innovations herein.

FIG. 7 is a schematic diagram illustrating XRD detection and CT detection that are implemented on two different liquid planes. As illustrated in FIG. 7, the X-rays emitted from the radiation source are divided into two parts with limitation of the primary collimator: rays that are deviated in the direction of the Z-axis and rays parallel to the X-axis. Here, the rays parallel to the X-axis are incidents rays for CT detection and may form a parallel beam or a fan-beam. The rays that are deviated in the direction of the Z-axis are incident rays for XRD detection and may include a plurality of pencil beam rays that may form a parallel beam or a fan-beam. Each incident ray for XRD detection corresponds to a XRD detection/scattering collimation module. With limitation of the scattering collimator, the XRD detector may measure energy spectra of a transmitted ray and scattered rays at a fixed scattering angle. The scattered rays at the same scattering angle from the same scattering center form a cone surface and get into the XRD detector via the scattering collimator.

As illustrated in FIG. 7, the scattering centers for XRD detection and the tomography for CT detection are at a certain distance away from each other in the direction of the Z-axis. The distance may be far enough to ensure that the extending lines of the scattered rays for XRD detection do not intersect with the incident ray for CT detection (i.e., the incident ray within the CT detection plane), as illustrated in FIG. 3. The distance may also be relatively close, in this case the scattered rays whose extending line intersects with the incident ray for CT detection will not be utilized for XRD detection.

As illustrated in FIG. 7, the X-rays spread out in the direction of the Y-axis, and the scattering centers for XRD detection may also spread along the direction of the Y-axis. The object stage rotates with the container containing the liquid carried thereon, in this way, on one hand the requirements of CT imaging may be satisfied, and on the other hand the plurality of scattering centers may scan the whole liquid plane so that the requirements of XRD imaging may be satisfied (i.e., XRD information of various points on the whole liquid plane may be obtained).

Figure 8:
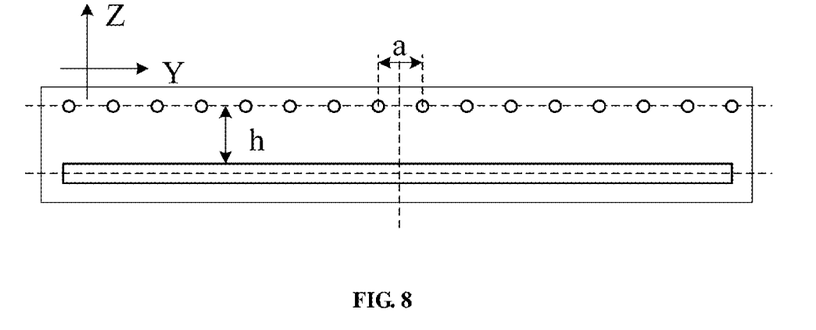
FIG. 8 is a schematic diagram illustrating a first example of a primary collimator that is utilized when XRD detection and CT detection are implemented on two different liquid planes, according to one or more aspects consistent with innovations herein.

FIG. 8 is a schematic diagram illustrating a first example of a primary collimator that is utilized when XRD detection and CT detection are implemented on two different liquid planes. As illustrated in FIG. 8, incident rays for CT detection may pass through a slit in a lower place of the primary collimator to form a fan-beam. In other embodiments, the slit may be substituted by a plurality of apertures, which may form a parallel beam when the radiation source is a distributed radiation source. The incident rays for XRD detection may pass through the apertures on the primary collimator to form a pencil beam. The apertures are on a same straight line parallel to the Y-axis and are, in the direction of the Z-axis, at a certain distance (h, which may be considered as a height difference in the Z-axis direction or an opening angle relative to the radiation source) away from the slit in the lower place. The apertures are equally spaced (a, which may be considered as a lateral distance in the direction of the Y-axis or an opening angle relative to the radiation source) in the direction of the Y-axis.

Figure 9:
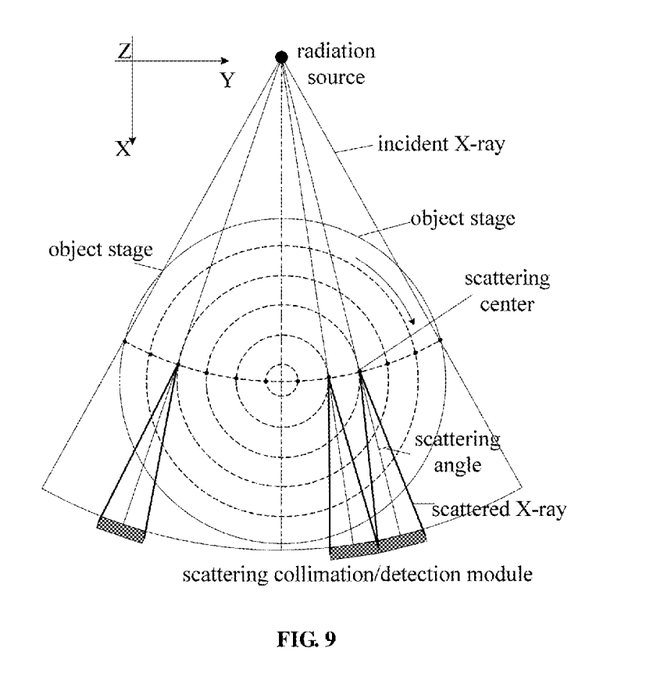
FIG. 9 is a schematic diagram illustrating XRD detection that is implemented by utilizing the primary collimator illustrated in FIG. 8, according to one or more aspects consistent with innovations herein.

FIG. 9 is a schematic diagram illustrating XRD detection that is implemented by utilizing the primary collimator illustrated in FIG. 8. For simplicity of description and drawing, incident rays for the XRD detection are illustrated as parallel to the X-Y plane, that is, the incident-ray plane overlays with the XRD detection plane. In practical, as illustrated in FIG. 7, there is a certain angle between the incident rays for the XRD detection and the XRD detection plane (i.e., the plane scanned by scattering centers), and the scattering centers are distributed on an intersecting line of the incident-ray plane and the detection plane. The basic principle, idea and system function herein are consistent, and the drawing of FIG. 9 will not affect the understanding. Within the XRD detection plane and with the limitation of the primary collimator (the primary collimator is located between the radiation source and the object stage, and is not shown in the figure), the incident rays for the XRD detection are divided into several pencil beam rays that form a fan. In other embodiments, a distributed radiation source may be utilized, and the pencil beam rays may form a parallel beam, etc. The scattering collimator and the detector corresponding to the scattering collimator may form a scattering collimation/detection module, wherein each module corresponds to a pencil beam ray, and the XRD detector may measure scattered rays at a certain angle (distributed on the cone surface) and transmitted rays with the limitation of the scattering collimator. The scattering centers are distributed in the detection area, i.e., the liquid plane above the object stage and parallel to the X-Y plane and between the radiation source and the detector.

As illustrated in FIG. 9, the scattering centers are distributed on an arc passing through the center of the detection area. The scattering collimation/detection module may be provided at a certain distance away from a corresponding scattering center along a corresponding incident ray, wherein the distance is relevant to the radiuses of the circular rings, the scattering angle, etc.

The object stage rotates with the container containing the liquid carried thereon in the direction indicated with the arrow or in the reverse direction, such that as shown by the dotted circle in FIG. 9, the scattering centers scan the whole liquid plane and acquire XRD information of respective points within the liquid plane. Energy spectra of every ray that are measured at the same time may be used for correcting the energy spectrum of the XRD image.

Figure 10:
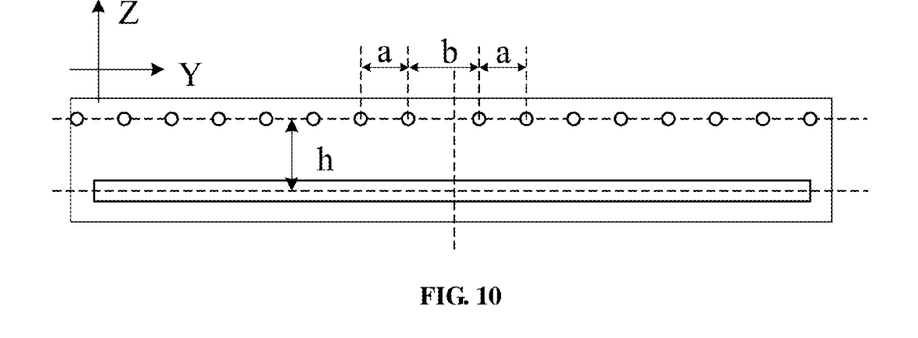
FIG. 10 is a schematic diagram illustrating a second example of a primary collimator that is utilized when XRD detection and CT detection are implemented on two different liquid planes, according to one or more aspects consistent with innovations herein.

FIG. 10 is a schematic diagram illustrating a second example of a primary collimator that is utilized when XRD detection and CT detection are implemented on two different liquid planes. The structure of the primary collimator as illustrated in FIG. 10 is similar as that illustrated in FIG. 8, and the only difference is the following: as to the apertures corresponding to the XRD detection, the apertures on the left side and the apertures on the right side are both equally spaced, while there is an offset on the left side with respect to the right side. As shown in the figure, the distance between the two apertures in the middle is b rather than a, and the value of b may be 1.5 times the value of a, so that scan tracks of the scattering centers may be staggered and the spatial resolution of the XRD detection may be improved.

Figure 11:
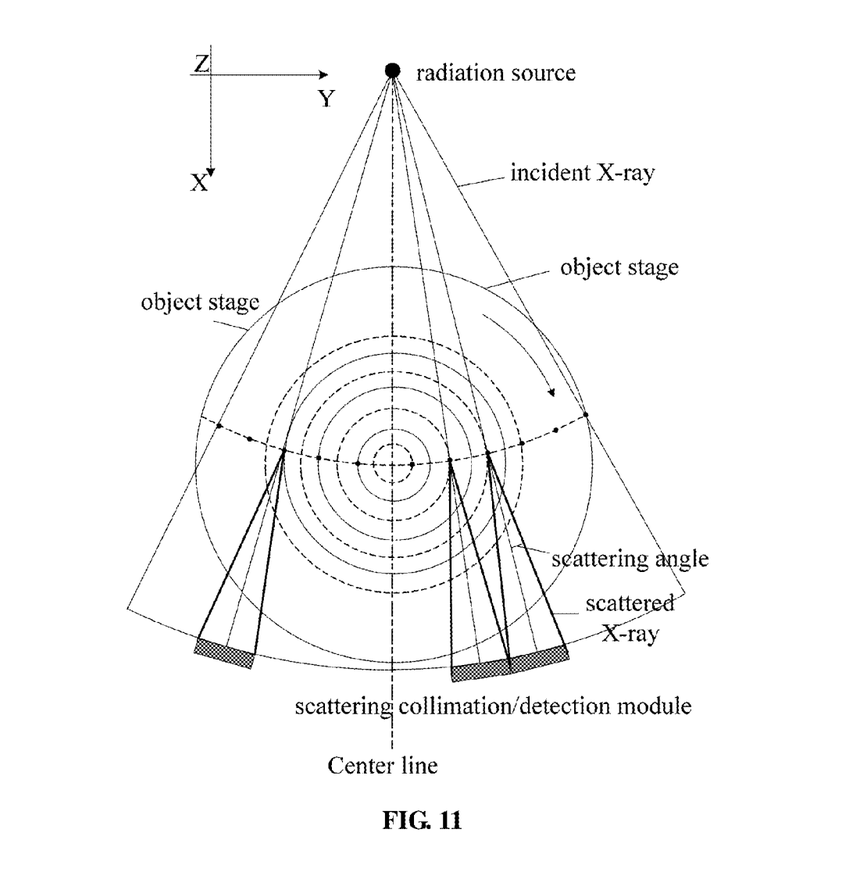
FIG. 11 is a schematic diagram illustrating XRD detection that is implemented by utilizing the primary collimator illustrated in FIG. 10, according to one or more aspects consistent with innovations herein.

FIG. 11 is a schematic diagram illustrating XRD detection that is implemented by utilizing the primary collimator illustrated in FIG. 10. As illustrated in FIG. 11, a center line divides the XRD detection plane into two parts: a left part and a right part. In the right part, the scattering centers are equidistant from each other or the rays emitted by the radiation source are equiangular from each other, and detection tracks as illustrated by dashed lines may be formed within the detection plane during rotation of the object. In the left part, the scattering centers are also equidistant from each other or the rays emitted by the radiation source are equiangular from each other, and the distance between two neighboring scattering centers is equal to that in the right part, but there is an offset at the scattering center next to the right part, so that detection tracks of the scattering centers in the left part are staggered as compared with the detection tracks in the right part, as shown by the solid line circles in the figure. This design may reduce sampling intervals within the XRD detection plane and thus improve the spatial resolution of XRD detection.

Figure 12:
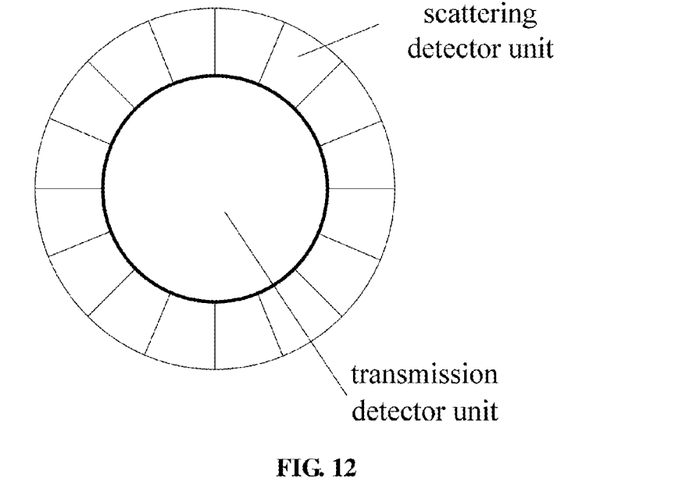
FIG. 12 is a schematic diagram illustrating a first example of a XRD detector used in the system for liquid detection illustrated in FIG. 2, according to one or more aspects consistent with innovations herein.
Figure 13:
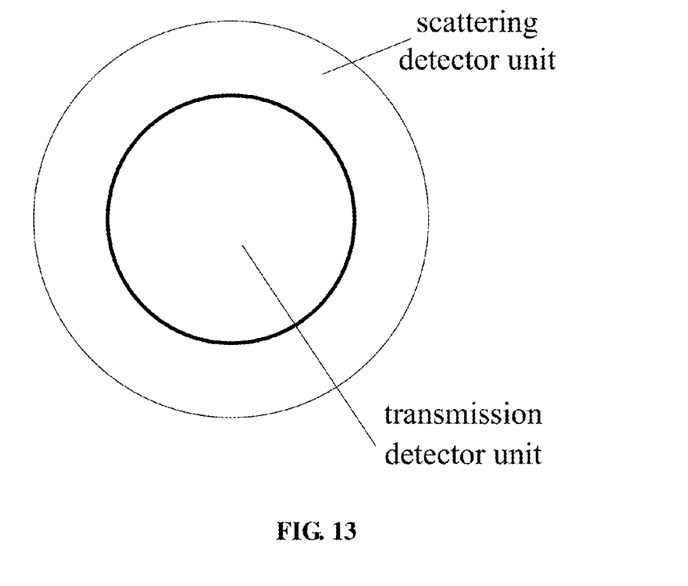
FIG. 13 is a schematic diagram illustrating a second example of a XRD detector used in the system for liquid detection illustrated in FIG. 2, according to one or more aspects consistent with innovations herein.

FIG. 12 and FIG. 13 are schematic diagrams respectively illustrating a first example and a second example of a XRD detector used in the system for liquid detection illustrated in FIG. 2. In the example illustrated by FIG. 12, the XRD detector is divided into two parts: a transmission detector unit and a scattering detector unit. The intermediate circular area is the transmission detector unit, which is configured to measure energy spectrum of a transmitted ray, wherein the transmission detector unit may be of other shapes than a circle. The transmission detector unit may be a single-pixel detector, or a multi-pixel detector. The scattering detector unit is distributed in the outer ring of the transmission detector unit, and includes several pixels that output energy spectra of scattered rays in different directions. In the example as illustrated by FIG. 13, the transmission detector unit is the same as that illustrated in FIG. 12, while the scattering detector unit is a whole pixel and outputs a summation of energy spectra of all scattered rays.

Here, the uniformity of liquid is fully utilized, a liquid plane(s) of interest is selected by DR irradiating and the XRD detection and the CT detection are implemented on the selected liquid plane(s). The radiation source is shared by the XRD detection and the CT detection, in which the scan of the selected liquid plane(s) is completed by rotating the object. The substances contained in the liquid may be accurately identified by combining the CT image with the XRD image, so the liquid security check may be implemented. The CT detection and the DR detection may be implemented by utilizing a same radiation source and a same detector. The radiation source is shared by the XRD detection, the CT detection, and the DR detection, so the system size and the number of radiation sources required may be reduced compared to a multi-stage liquid detection system. In addition, the CT detection and the XRD detection in the system for liquid detection according to the embodiments of the disclosure only require a column of (or a plurality of) detector units, so the amount of detectors may be reduced as compared with a planar array of detectors, so the cost may be reduced. The pencil-conical surface detection method greatly improves signal strength, and the whole area of a liquid plane may be measured by rotating the object. XRD detection and CT detection may be performed simultaneously, which saves measuring time for the whole liquid detection system.

It will be appreciated that the inventive concept is not limited to the exact configuration and process that have been described above and illustrated in the accompanying drawings. And detailed descriptions of known method and techniques are omitted herein for simplicity. A number of specific steps are described and illustrated in the above embodiments as examples. However, the method and process of the present invention is not limited to the specific steps described and illustrated, and various changes, modifications and additions can be made or the order of the steps may be changed by the skilled in the art after understanding the spirit of the invention.

The selection of the liquid plane(s), the process of utilizing DR information, CT information and XRD information acquired by a detector for DR imaging, CT imaging and XRD imaging, and the process of generating a substance identification result for the liquid based on a CT image and a XRD image may be implemented by functional blocks not shown in the figures. Herein these blocks may be implemented in hardware, software, firmware of the combinations thereof. The hardware may include, for example, an electronic circuit, an application specific integrated circuit (ASIC), an appropriate firmware, plug-in component, function card, etc. The software may include, for example, a program or a code segment to perform the tasks required. The program or the code segment may be stored in a machine-readable medium, or be transmitted in a data signal carried by a carrier wave over a transmission medium or a communication link. The machine-readable medium may include any medium that can store or transmit information. The machine-readable medium may include, for example, an electronic circuit, a semiconductor memory device, ROM, flash memory, erasable ROM (EROM), floppy disk, CD-ROM, optical disk, hard disk, fiber optic medium, radio frequency (RF) link, etc. The code segment may be downloaded via networks such as internet, intranet, etc.

The invention may be embodied in other specific forms without departing from the spirit and essential characteristics. For example, an algorithm described in a specific embodiment may be modified without departing from the spirit of the invention. Accordingly, various aspects of the embodiments are to be considered as illustrative rather than restrictive. It is intended that the scope of the invention only be limited by the appended claims, and all modifications, equivalent substitutions, and improvements that fall within the spirit and principles of the disclosure should be included in the scope of protection of this disclosure.

What is claimed is:

1. A method for liquid detection, comprising:
implementing CT imaging and XRD imaging on one or more liquid planes of liquid contained in a container at the same time by rotating the container so that X-rays from a same radiation source scan a whole area of each of the one or more liquid planes, wherein the X-rays from the radiation source are separated into X-rays for the CT imaging and X-rays for the XRD imaging; and
generating a substance identification result for the liquid contained in the container based on a CT image and a XRD image, wherein the CT imaging and the XRD imaging are implemented on a same liquid plane or different liquid planes.

2. The method for liquid detection according to claim 1, further comprising:
forming, by a primary collimator, X-rays for the CT imaging and X-rays for the XRD imaging from the X-rays from the radiation source.

3. The method for liquid detection according to claim 1, further comprising:
implementing the XRD imaging by utilizing, by scattering collimators, scattered rays, which are generated when the X-rays from the radiation source reach scattering centers, at one or more particular scattering angles.

4. The method for liquid detection according to claim 1, further comprising:
implementing DR imaging for the liquid contained in the container by utilizing the radiation source, and selecting the one or more liquid planes based on a DR image.

5. The method for liquid detection according to claim 4, wherein the DR imaging is implemented by utilizing the X-rays for the CT imaging.

6. The method for liquid detection according to claim 2, wherein when the CT imaging and the XRD imaging are implemented on the same liquid plane, a CT slit or apertures for forming the X-rays for the CT imaging and XRD apertures for forming the X-rays for the XRD imaging on the primary collimator are on a same straight line within a same plane.

7. The method for liquid detection according to claim 2, wherein when the CT imaging and the XRD imaging are implemented on different liquid planes, a CT slit or apertures for forming the X-rays for the CT imaging and XRD apertures for forming the X-rays for the XRD imaging on the primary collimator are on different straight lines at a predetermined distance away from each other within a same plane.

8. The method for liquid detection according to claim 3, further comprising:
measuring, by the scattering collimators, transmitted energy spectra of transmitted rays generated when the X-rays from the radiation source pass through the scattering centers, and correcting the XRD image based on data of the transmitted energy spectra.

9. The method for liquid detection according to claim 1, wherein the radiation source is a single point radiation source or a distributed radiation source.

10. A system for liquid detection, comprising:
a radiation source configured to emit X-rays;
a primary collimator provided at the downstream of the radiation source and configured to separate the X-rays from the radiation source into X-rays for CT imaging and X-rays for XRD imaging;
a CT imaging apparatus configured to implement CT imaging by utilizing the X-rays for CT imaging;
a XRD imaging apparatus configured to implement XRD imaging by utilizing the X-rays for XRD imaging;
a carrying apparatus configured to rotate a container containing liquid, so that the X-rays from the radiation source scan a whole area of each of one or more liquid planes of the liquid contained in the container, wherein
the CT imaging apparatus and the XRD imaging apparatus implement the CT imaging and the XRD imaging on the one or more liquid planes at the same time, and a CT image and an a XRD image are utilized to generate a substance identification result for the liquid contained in the container.

11. The system for liquid detection according to claim 10, wherein the XRD imaging apparatus comprises one or more XRD detection/scattering collimation modules, wherein any of the one or more XRD detection/scattering collimation modules comprises:
a XRD detector configured to receive scattered rays via a scattering collimator, and
the scattering collimator provided at the upstream of the XRD detector and configured to allow only a part of the scattered rays, which are generated when one of the X-rays for XRD imaging reaches a scattering center, to be received by the XRD detector.

12. The system for liquid detection according to claim 10, wherein the primary collimator comprises a CT slit or apertures for forming the X-rays for CT imaging and XRD apertures for forming the X-rays for XRD imaging, and the CT slit or apertures and the XRD apertures are on a same straight line within a same plane or on two different straight lines at a predetermined distance away from each other within the same plane.

13. The system for liquid detection according to claim 12, wherein the XRD apertures are a series of apertures on the same straight line.

14. The system for liquid detection according to claim 12, wherein when the CT slit or apertures and the XRD apertures are on two different straight lines at the predetermined distance away from each other within the same plane, there is a predetermined offset between the XRD apertures on the left side of the primary collimator and the XRD apertures on the right side of the primary collimator.

15. The system for liquid detection according to claim 11, wherein the scattering collimator is further configured to allow only the scattered rays, which are generated when one of the X-rays for XRD imaging reaches the scattering center, at one or more particular scattering angles to be received by the XRD detector.

16. The system for liquid detection according to claim 11, wherein the scattering collimator is further configured to allow a transmitted ray, which is generated when one of the X-rays for XRD imaging passes through the scattering center, to be received by the XRD detector.

17. The system for liquid detection according to claim 16, wherein the XRD detector comprises a transmission detector unit and one or more scattering detector units, wherein the one or more scattering detector units are distributed around the transmission detector unit.

18. The system for liquid detection according to claim 10, wherein the CT imaging apparatus is further configured to implement DR imaging by utilizing the X-rays for CT imaging, wherein the CT imaging apparatus and the XRD imaging apparatus implement the CT imaging and the XRD imaging on the one or more liquid planes, which are selected based on a DR image.

* * * * *